United States Patent [19]

Warriner

[11] Patent Number: Plant 5,261

[45] Date of Patent: Jul. 24, 1984

[54] ROSE PLANT '80-20545 JACIF'

[75] Inventor: William A. Warriner, Tustin, Calif.

[73] Assignee: Jackson & Perkins Company, Medford, Oreg.

[21] Appl. No.: 443,022

[22] Filed: Nov. 19, 1982

[51] Int. Cl.[3] ..... A01H 5/00

[52] U.S. Cl. ..... Plt./25

[58] Field of Search ..... Plt./25

*Primary Examiner*—James R. Feyrer

*Attorney, Agent, or Firm*—Klarquist, Sparkman, Campbell, Leigh & Whinston

[57] ABSTRACT

A floribunda rose variety having "salmon" bud and bloom color, petal and flower form similar to variety Mercedes, good resistance to rose powdery mildew, straight and stiff stems, and little or no fragrance.

1 Drawing Figure

This present invention relates to a new and distinct variety of rose plant of the floribunda class which was originated by me by crossing the variety Mercedes with the variety Marina.

The primary objective of this breeding was to produce a new rose variety particularly for use as a cut flower variety with growth characteristics similar to both parents and of a different color. This objective was substantially achieved along with other desirable improvements as evidenced by the following unique combination of characteristics which are outstanding in the new variety and which distinguish it from its parents, as well as from all other varieties of which I am aware:

1. A "salmon" color in bud and bloom, close to R.H.S. Red 37B.
2. Petal and flower form similar to variety Mercedes.
3. Good resistance to rose powdery mildew.
4. Straight, stiff stems suitable for use as a cut flower.
5. Little or no fragrance.

Asexual reproduction of this new variety by budding, as performed at Wasco, Calif., and grafting at Irvine, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Mercedes.

*Pollen parent.*—Marina.

Classification:

*Botanical.*—Rosa hybrid.

*Commercial.*—Floribunda.

FLOWER

Observations made from specimens grown in a greenhouse at Irvine, Calif. in October, 1982.

Blooming habit: Continuous.

Bud:

*Size.*—1" when petals start to unfurl.

*Form.*—Pointed ovoid.

*Color.*—When sepals first divide, Near Red Group 37A. When half blown; upper side of petals Red Group 37B; lower side of petals Red Group 37B.

*Sepals.*—Color: Outer surface Green 138B. Texture — very few glands near base of sepals. Three appendaged sepals normally appendaged, edges with stipitate glands. Two unappendaged sepals hairy edged.

*Receptacle.*—Color: Green 138B. Shape: Funnel. Size: Small. Surface: Slightly hairy.

*Peduncle.*—Length: Short. Surface: Glandular. Color: Light green. Strength: Stiff, erect.

*Opening.*—Petal edges curl back.

Bloom:

*Size.*—Small.

*Borne.*—Singly or several together.

*Stems.*—Medium to short; 10" to 18" in greenhouse.

*Form.*—When first open, high center. Permanence: Retains its form to the end.

*Petalage.*—Number of petals under normal conditions: 30–35.

*Color.*—Center of flower: Upper side of petals Red Group 37B; reverse side of petals Red Group 37C; base of petals Yellow Group 8B. General tonality from a distance Red Group 37B.

*Variegations.*—None.

*Discoloration.*—General tonality at end of first day: No change. Third day: Red Group 37C.

*Fragrance.*—Slight.

Petals:

*Texture.*—Thick.

*Shape.*—Round.

*Form.*—Edges slightly quilled.

*Arrangement.*—Irregular. Petaloids in center, few.

*Persistence.*—Drop off cleanly.

*Lastingness.*—On the plant, very long. As cut flower, very long.

Reproductive parts:

*Anthers.*—Medium. Color: Yellow. Arrangement: Regular around styles.

*Filaments.*—Color: Yellow.

*Pollen.*—Lemon yellow.

*Styles.*—Color: Mostly white with pink tint.

*Stigmas.*—Color: White.

PLANT

Form: Bush.

Growth: Very vigorous, upright.

Foliage: Number of leaflets on normal mid-stem leaves: 5–7.

*Size.*—Medium.

*Quantity.*—Normal.

*Color.*—New foliage: Greyed Purple 183A. Old foliage: Green 137A.

Leaflets:

*Shape.*—Elliptic.

*Texture.*—Upper side: Semi-glossy.

*Edge.*—Serrated.

*Serration.*—Single, small.

*Petiole.*—Rachis: Color: Reddish. Underside: Prickles.

*Stipules.*—Long, bearded.

*Disease resistance.*—Resistant to mildew under normal growing conditions at Irvine, Calif. under greenhouse conditions.

Wood:

*New wood.*—Color: Reddish. Bark: Smooth.

*Old wood.*—Color: Green with corky streaks. Bark: Smooth.

Prickles:

*Quantity.*—On main stalks from base, ordinary to few. On laterals from stalk, ordinary to few.

*Form.*—Long, hooked downward slightly.

*Color when young.*—Brown.

*Position.*—Irregular.

Small prickles:

*Quantity.*—On main stalks, none. On laterals, none.

I claim:

1. A new and distinct variety of rose plant of the floribunda class, substantially as herein shown and described, characterized particularly as to novelty by the unique combination of salmon pink buds and blooms, high-centered flower form, similar to variety Mercedes, resistance to rose powdery mildew, straight stems and lack of fragrance.

* * * * *

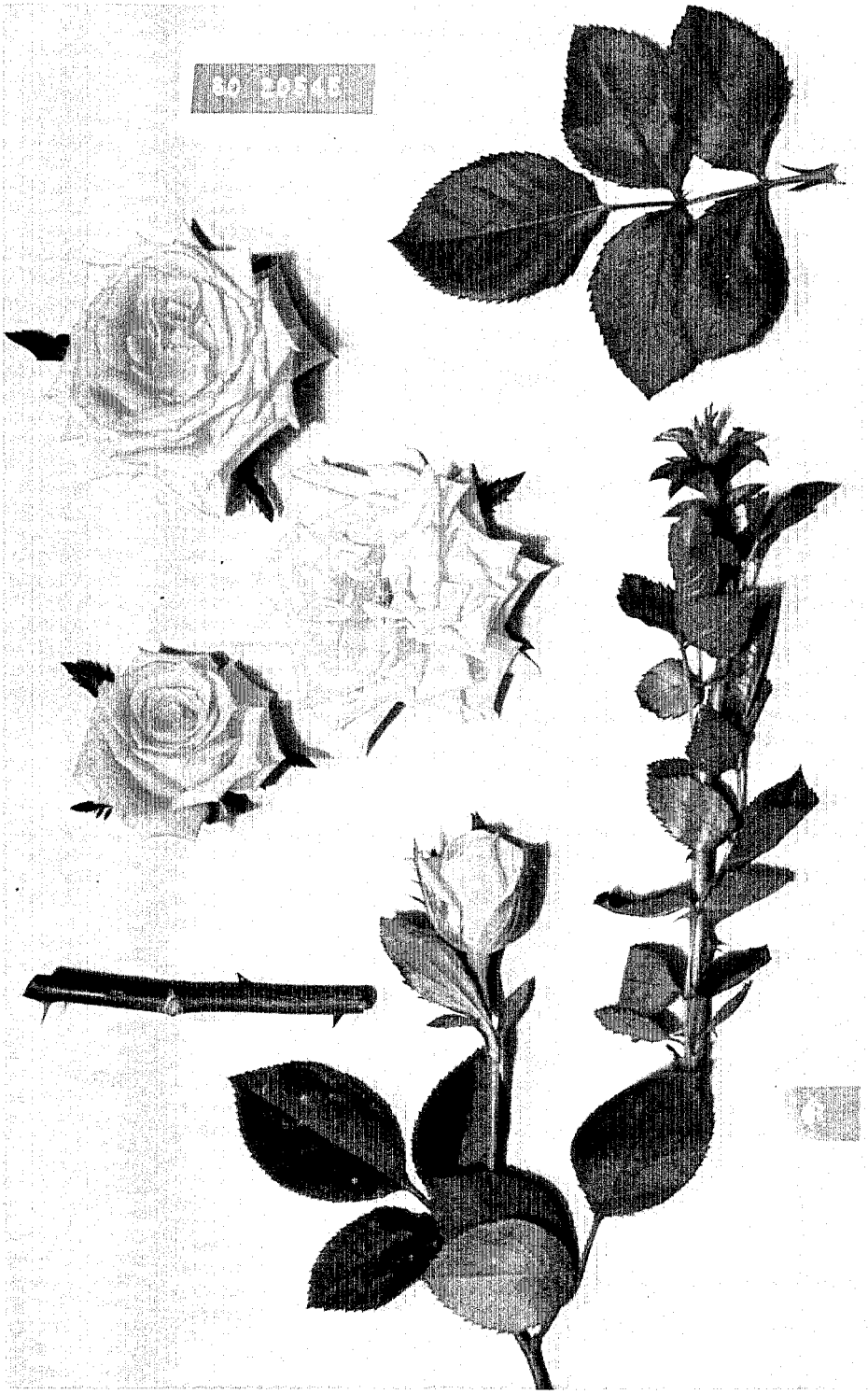
LO LOEDE